United States Patent
Deligianni

(10) Patent No.: US 12,201,425 B1
(45) Date of Patent: Jan. 21, 2025

(54) STRESS BIOMARKER AND HEALTH INDICATOR SYSTEM

(71) Applicant: SENSE4ME INC., Upper Saddle River, NJ (US)

(72) Inventor: Hariklia Deligianni, Palm Beach, FL (US)

(73) Assignee: Sense4me Inc., Upper Saddle River, NJ (US)

( * ) Notice: Subject to any disclaimer, the term of this patent is extended or adjusted under 35 U.S.C. 154(b) by 0 days.

(21) Appl. No.: 16/460,275

(22) Filed: Jul. 2, 2019

Related U.S. Application Data

(60) Provisional application No. 62/693,068, filed on Jul. 2, 2018.

(51) Int. Cl.
*A61B 5/16* (2006.01)
*A61B 5/00* (2006.01)
(Continued)

(52) U.S. Cl.
CPC ............... *A61B 5/165* (2013.01); *A61B 5/01* (2013.01); *A61B 5/02055* (2013.01); *A61B 5/1451* (2013.01); *A61B 5/14546* (2013.01); *A61B 5/1455* (2013.01); *A61B 5/1477* (2013.01); *A61B 5/24* (2021.01); *A61B 5/4803* (2013.01);
(Continued)

(58) Field of Classification Search
CPC ..... A61B 5/165; A61B 5/1477; A61B 5/4803; A61B 5/02055; A61B 5/04001; A61B 5/14546; A61B 5/1455; A61B 5/741; A61B 5/1451; A61B 5/486; A61B 5/4836; A61B 5/01; A61B 5/02416; A61B 5/4035; A61B 5/0531; A61B 2562/0204
See application file for complete search history.

(56) References Cited

U.S. PATENT DOCUMENTS

| | | | |
|---|---|---|---|
| 10,390,755 B2 * | 8/2019 | Goodall | A61B 5/00 |
| 2016/0022180 A1 * | 1/2016 | Joseph | A61B 5/14532 600/317 |

(Continued)

FOREIGN PATENT DOCUMENTS

| | | | | |
|---|---|---|---|---|
| AU | 2014337142 A1 * | 5/2016 | | A61B 10/0064 |
| JP | 5658571 B2 | 1/2015 | | |

OTHER PUBLICATIONS

Zhao et al, A Flexible Interdigital Electrode Used in Skin Penetration Promotion and Evaluation with Electroporation and Reverse Iontophoresis Synergistically, Sensors 2018, 18, 1413, published May 4, 2018. (Year: 2018).*

(Continued)

*Primary Examiner* — Gary Jackson
*Assistant Examiner* — Ranjani Mari Sundaresan
(74) *Attorney, Agent, or Firm* — Occhiuti & Rohlicek LLP

(57) ABSTRACT

A point-of-use analysis with biosensors for peripheral body fluids (e.g., saliva, urine and sweat) and interstitial fluid provides measurements that gain insights to the stress response and inflammation. These measurements may be used in a closed-loop approach in which they are analyzed, and a subject's progress is measured and therapy controlled according to that progress. The point-of-use biosensors provide an opportunity to better understand the effects of stress in real-time and during normal life activities. The digital point-of-use biosensor device enable personalized medicine for many disease conditions.

23 Claims, 6 Drawing Sheets

(51) Int. Cl.
| | |
|---|---|
| A61B 5/01 | (2006.01) |
| A61B 5/0205 | (2006.01) |
| A61B 5/024 | (2006.01) |
| A61B 5/0531 | (2021.01) |
| A61B 5/145 | (2006.01) |
| A61B 5/1455 | (2006.01) |
| A61B 5/1477 | (2006.01) |
| A61B 5/24 | (2021.01) |

(52) U.S. Cl.
CPC ............ *A61B 5/4836* (2013.01); *A61B 5/486* (2013.01); *A61B 5/741* (2013.01); *A61B 5/02416* (2013.01); *A61B 5/0531* (2013.01); *A61B 5/4035* (2013.01); *A61B 2562/0204* (2013.01)

(56) References Cited

U.S. PATENT DOCUMENTS

| | | | | |
|---|---|---|---|---|
| 2016/0367188 | A1* | 12/2016 | Malik | G16H 40/67 |
| 2017/0112671 | A1* | 4/2017 | Goldstein | H04R 25/554 |
| 2017/0164876 | A1* | 6/2017 | Hyde | A61N 1/36003 |
| 2017/0251985 | A1* | 9/2017 | Howard | G16H 70/60 |
| 2018/0121784 | A1* | 5/2018 | Ichiboshi | G16H 10/20 |

OTHER PUBLICATIONS

Hui TKL, Sherratt RS. Coverage of Emotion Recognition for Common Wearable Biosensors. Biosensors. 2018; 8(2):30. https://doi.org/10.3390/bios8020030 (Year: 2018).*

Koh et al. A soft, wearable microfluidic device for the capture, storage, and colorimetric sensing of sweat. Sci Transl Med. Nov. 23, 2016;8(366):366ra165. doi: 10.1126/scitranslmed.aaf2593. PMID: 27881826; PMCID: PMC5429097 (Year: 2016).*

G. P. Chrousos, P.W. Gold, "The Concepts of Stress and Stress System Disorders: Overview of Physical and Behavioral Homeostasis," JAMA. 1992;267(9):1244-1252.

C. Tsigos, G.P. Chrousos, "Hypothalamic-pituitary-adrenal axis, neuroendocrine factors and stress," J. Psycho-somatic Research (2002) 53:865-871.

G.P. Chrousos, Stress and disorders of the stress system, Nature Reviews Endocrinology, 5, 374-381 (2009).

P.W. Gold, G.P. Chrousos, "Organization of the stress system and its dysregulation in melancholic and atypical depression: high vs low CRH/NE states," Molecular Psychiatry, 7, 254-275 (2002).

P.W. Gold, "The organization of the stress system and its dysregulation in depressive illness," Molecular Psychiatry, 20:32-47(2015).

Dahlgren, A.; Kecklund, G.; Theorell, T.; Akerstedt, T. Day-to-day variation in saliva cortisol-relation with sleep, stress and self-rated health. Biol. Psychol. 2009, 82 (2), 149-155.

Zora D., C. E. Bird, A. Furumoto-Dawson , G. H. Rauscher , M. T. Ruffin IV , R. P. Stowe, K. L. Tucker, C. M. M. Biomarkers of Psychological Stress in Health Disparities Research. Open Biomark. J. 2008, 1, 7-19.

Dimsdale, J. E. Psychological Stress and Cardiovascular Disease. Journal of the American College of Cardiology. 2008, 51 (13), 1237-1246.

Chaby, L. E.; Cavigelli, S. A.; Hirrlinger, A. M.; Caruso, M. J.; Braithwaite, V. A. Chronic unpredictable stress during adolescence causes long-term anxiety. Behav. Brain Res. 2015, 278, 492-495.

Naumova, E. A; Sandulescu, T.; Bochnig, C.; Khatib, P. Al; Lee, W.-K.; Zimmer, S.; Arnold, W. H. Dynamic changes in saliva after acute mental stress. Sci. Rep. 2014, 4, 4884.

* cited by examiner

STRESS BIOMARKER AND HEALTH INDICATOR SYSTEM

CROSS-REFERENCE TO RELATED APPLICATIONS

This application claims the benefit of U.S. Provisional Application No. 62/693,068 filed on Jul. 2, 2018.

BACKGROUND

This invention relates to a system and method for measuring stress biomarkers and health indicators.

According to the World Health Organization (WHO) mental health is pervasive affecting 1 in 4 adults throughout their lifespan. Mental health is defined by WHO as "a state of well-being in which every individual realizes his or her own potential, can cope with the normal stresses of life, can work productively and fruitfully, and is able to make a contribution to her or his community". This state, however, is disrupted in one of every four individuals during their lifetimes.

In 2010, mental and substance abuse disorders accounted for about 10% of the global burden of disease and were the leading cause of years lived with disability among all disease groups. The economic cost of mental disorders is devastating estimated to be 2.5 T $US using a human capital approach and its impact on economic growth is 16 T $US. The economic impact is higher than any chronic somatic disease such as cancer, diabetes and chronic respiratory disease combined! Depressive disorders affect more than 300 million people and is the leading cause of disability. Worldwide, bipolar disorder affects 60 million people, and schizophrenia impacts more than 21 million.

Beyond this, stigmatization and misconceptions of both mental and addictive disorders seem to play a major role. Very often the public seems to believe that mental and substance use disorders are not "real diseases", that they cannot be treated effectively, and that people affected are at least partly responsible. As a consequence, societies are willing to spend much more on somatic diseases than on mental disorders, even though both disability and economic costs are at least as high as those caused by somatic conditions. In addition, the United States faces a tremendous substance abuse and addiction epidemic. Furthermore, the development and implementation of sound and effective early diagnostic and monitoring treatments outside the doctor's office and during daily living are lacking.

As a response to external and or internal stressors, the human body produces a stress response mediated with the release of hormones and catecholamines in the central nervous system (CNS) and in the periphery. Behavioral and physiological adaptive response to stress is a function of both genetic and environmental factors. Changes in the ability to effectively adapt to stressors and chronic hyper or hypo activation of the stress system can lead to disease. Cortisol is one of the hormones released with the stress response. For patients with depression, changes in the blood plasma cortisol, epinephrine and norepinephrine during the circadian cycle is evident. After ECT treatment, hormones and catecholamines followed a circadian cycle with levels similar to the healthy subjects. Furthermore, a link between elevated cortisol levels in bodily fluids such as saliva, and anxiety has been identified.

Current methods to diagnose stress dysregulation, depression and anxiety include interviews, counseling, and self-questionnaires. These methods are purely qualitative and can even introduce bias in the diagnosis. Moreover, techniques that rely on blood analysis, require longer times to perform the analysis and need access to laboratory equipment to perform the tests. The most commonly used methods for the estimation of free cortisol are limited to laboratory techniques that are laborious, time-consuming, expensive, and cannot be implemented at the point-of-use (POU). Effective measurement methods for cortisol detection involves liquid chromatograph mass spectrometry (LC/MS), enzyme-linked immunosorbent assay (ELISA), electrochemiluminescence immunoassay (ECLIA), and surface plasmon resonance (SPR).

Moreover, current techniques only provide a snapshot of the cortisol levels of samples submitted in a diagnostic lab and do not provide a true representation of the cortisol variations that a subject undergoes in an environment that triggers cortisol generation or suppression. Hence, real-time monitoring of cortisol levels is highly desired to obtain valuable diagnostic information that could assist doctors in better diagnosis and treatment of stress-related conditions.

SUMMARY

In one aspect, in general, a point-of-use (POU) analysis with biosensors for peripheral body fluids (saliva, urine and sweat) and interstitial fluid provides measurements that gain insights to the stress response and inflammation. These measurements may be used in a closed-loop approach in which they are analyzed, and a subject's progress is measured and therapy controlled according to that progress. The point-of-use biosensors provide an opportunity to better understand the effects of stress in real-time and during normal life activities. The digital point-of-use biosensor device enable personalized medicine for many disease conditions.

Implementations of the system enable frequent measurements, in real-time, non-invasively by sampling stress biomarkers such as cortisol, epinephrine, norepinephrine, neuropeptide (NPY) and inflammatory cytokines such as TNF-a, IL-1, IL-6 in saliva, sweat, urine and minimally invasively in the interstitial fluid.

Real-time, personalized, actionable insights into the user's wellbeing and health by monitoring multimodal inputs are enabled with the use of appropriate algorithms and fusion of different modalities such as the biomarkers of stress and inflammation, skin conductance which is indicative of arousal and activation or de-activation of the sympathetic/parasympathetic nervous system and the hypothalamic pituitary axis (HPA) and conversational data to be part of the algorithms and to determine whether the user will need to consult a medical professional. Once the user has been diagnosed with a disease condition, the control system is used to monitor the effectiveness of the proposed therapy, i.e., psychotherapy, cognitive behavioral therapy, other behavioral therapy, intervention with drugs or neural stimulation. In addition, the delivery of conversational therapies is automated and delivered in real-time and on demand when the patient is not at the doctor's office.

The level of cortisol, epinephrine, norepinephrine, NPY, TNF-a, IL-1 and IL-6 during a 24 hr period is indicative of whether the treatment is effective. For example, cortisol secretion follows a circadian cycle. In the evening and during sleep, maintaining a low cortisol level is very important for health. Blood serum cortisol levels are typically between 4-16 µg/dl (100 nM-600 nM). It has been shown previously, that patients with melancholic depression maintain cortisol levels as high as 10 µg/dl (275 nM) in the evening during sleep compared to the healthy subjects who have cortisol levels during the same time period more than 2× lower (100 nM).

Based on the biomarker and other physiological values, the computer system may initiate a conversation with the patient to determine the probability of a specific disease condition such as melancholic depression or diabetes. The computer system has the option to engage in a conversation with the user in order to assign a higher probability to a specific disease condition. For example, if the night cortisol levels, the epinephrine, norepinephrine and the TNF-a, IL-1, IL-6 levels are higher than the healthy cohort, the system starts a conversation with the user. For example, the system asks questions such as "May I record our conversation" and receives consent to do so in order to start. The conversation may include questions such as "How are you?", "Please tell me how was your day?", "What happened?", "How is your mood?", "How is your sleep?", "Are you thirsty?", etc. and the system automatically processes the patient's verbal responses.

Most (95%) of the cortisol in the blood is bound. In peripheral body fluids sweat, saliva, urine, cortisol is in free form and as a result its concentration is 1-2 orders of magnitude lower than in the blood. Consequently, the devices and biosensors used for analysis of peripheral body fluids must have a very low limit of detection of less than 1 μg/ml. Furthermore, the biosensors operate with extremely small sample volumes of <10 μl suitable for sweat, saliva, urine and interstitial fluid analysis. The developed sensor has the following specifications 1) a sensor with 10-15 min response time or <20 min; 2) limit of detection 1 pg/ml or <5 pg/ml; 3) sample volume of 5 μl or <10 μl suitable for sweat, saliva, urine and interstitial fluid analysis and 4) accuracy of >=90%.

In an aspect, in general, a computer-controlled system is configured to monitor the health of an individual. The system includes a miniaturized nanotechnology-based electrochemical device for measuring biomarkers of stress and inflammation in peripheral fluids and in interstitial fluid. The system also includes a miniaturized nanotechnology-based optical method to determine levels stress and inflammation of the individual. The system further includes a conversational agent (e.g., an AI implemented subsystem for natural language interaction), and a means to measure skin conductance, temperature, heart rate and the response of the autonomous nervous system. The system is configured to compare the measurement against an ideal level for that individual and provide actionable feedback to the medical professional about the health of the individual and about his/her treatment.

Aspects can include one or more of the following features.

The monitoring is performed in real-time and on demand.

In response to the analysis of the biomarkers, skin conductance, temperature and heart rate, the system engages the individual into conversation in order to refine a recommendation to the medical professional.

The system implements an algorithm that determines recommendations for the individual based on these measurements.

The system includes a miniaturized SERS Raman spectroscopic apparatus to non-invasively determine stress and inflammatory cytokines where these measurements are input to the recommendation algorithm.

The system includes a cloud web link to connect to the person's medical history to use as input to the recommendation algorithm and/or connect to healthcare providers to record recommendations and progress over time The system is configured to monitor the effectiveness of the proposed therapy i.e. psychotherapy, cognitive behavioral therapy, other behavioral therapy, medication or neural stimulation.

The system is configured to deliver automated conversational therapies that can be delivered in real-time and on demand as prescribed by the healthcare professional.

Other features and advantages of the invention are apparent from the following description, and from the claims.

DESCRIPTION

Figure 1:
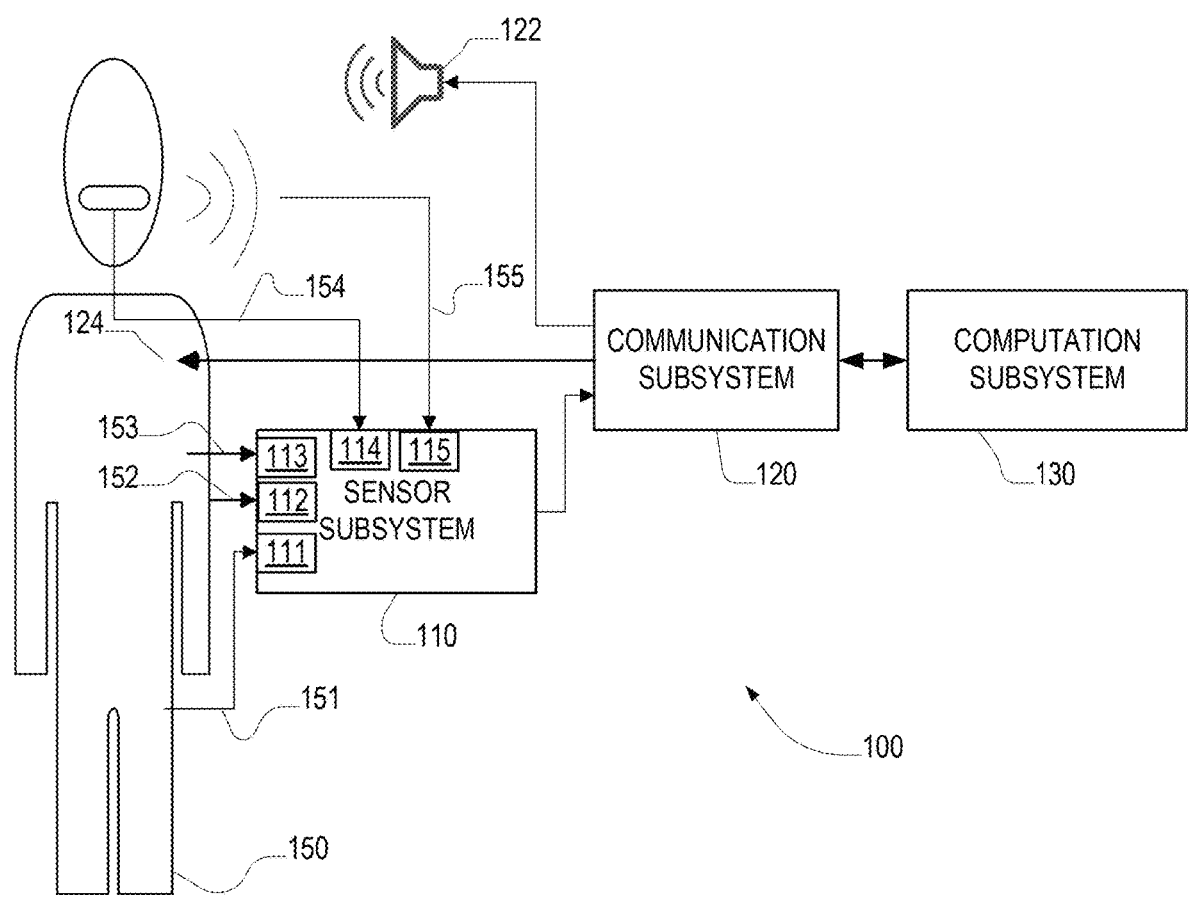
FIG. 1 is a schematic block diagram of a stress biomarker system.

Referring to FIG. 1, a system 100 monitors biomarkers of a subject 150, at least some being monitored continuously for periods of time, and provides feedback to the subject. The system 100 includes a sensor subsystem 110. In some examples, this subsystem is affixed to the subject's skin (e.g., on the arm), for example, with an adhesive or held in place with an adhesive covering (e.g., an adhesive bandage). Generally, the sensor subsystem 110 includes multiple separate sensors 111-115, each being used for a different mode of sensing. For example, a sensor 112 may sense characteristics 152 of the subject measurable at the skin such as electrical skin conductance or skin surface temperature. Sensor 113 may acquire biological fluid 153, such as sweat, blood, or interstitial fluid. For example, the sensor 113 may perform biochemical analysis to detect certain hormone levels. Sensors 114 and 111 may be used for saliva 154 and urine 151 (e.g., peripheral body fluids) respectively. In some embodiments, the subject collects the saliva or urine and places it on the sensor system that is affixed to the skin. In other embodiments, the sensor subsystem has separate modules, for example, with an in-mouth module to measure saliva and another sensor for measuring urine. Together sensors 111, 113, and 114 are consider body fluid sensors. In some examples, the body fluid sensor(s) (111, 113, 114) measure biomarkers such as cortisol, epinephrine, norepinephrine, neuropeptide (NPY) and inflammatory cytokines. A sensor 115 (e.g., a microphone) receives audio signals that may include speech or non-speech sounds 155 produced by the subject. Yet other locations for biosensing may be used, for example, using in-eye tear sensors, embedded sensors implanted in the body, or ingested sensors (e.g., "smart pills"). It should be understood that some embodiments, only a subset of the sensors illustrated in FIG. 1 are used.

The sensor system 110 interacts with a computation subsystem 130 via a communication subsystem 120. For example, the communication subsystem is hosted in a smartphone and communicates with the sensor subsystem using a wireless protocol (e.g., Bluetooth, inductive data transfer) and communicates with the computation subsystem 130 over a wide area network (e.g., cellular telephone and Internet). Very generally, the sensor subsystem 110 makes certain sensor measurements continuously or frequently, and in real time (i.e., with relatively low delay, e.g., seconds or minutes) passes the measured values to the computation system. The computation system implements a decision system, for example, using artificial intelligence (AI) techniques to detect a set of predefined conditions. In some cases, operation of the computation system causes feedback to be sent to the subject, for example, causing audio signals (e.g., voice signal) to be emitted from the communication subsystem 120 via a speaker 122. The feedback may also be via a physical input 124, for example, with automated delivery of electrical stimulus or possibly with automated delivery of a drug (e.g., with an automated drug delivery mechanism, e.g., pump). As discussed further below, in some examples, the computation system determines that further sensor data needs to be acquired to determine a condition of the subject, and the computation system causes the sensor system to make the required measurements, or alternatively, instructs the subject via the speaker to state certain measurements or perform certain speech tasks and collects the resulting audio measurements. In some examples, the audio output comprises automatically conversational therapy synthesized by the computational system.

Figure 2:
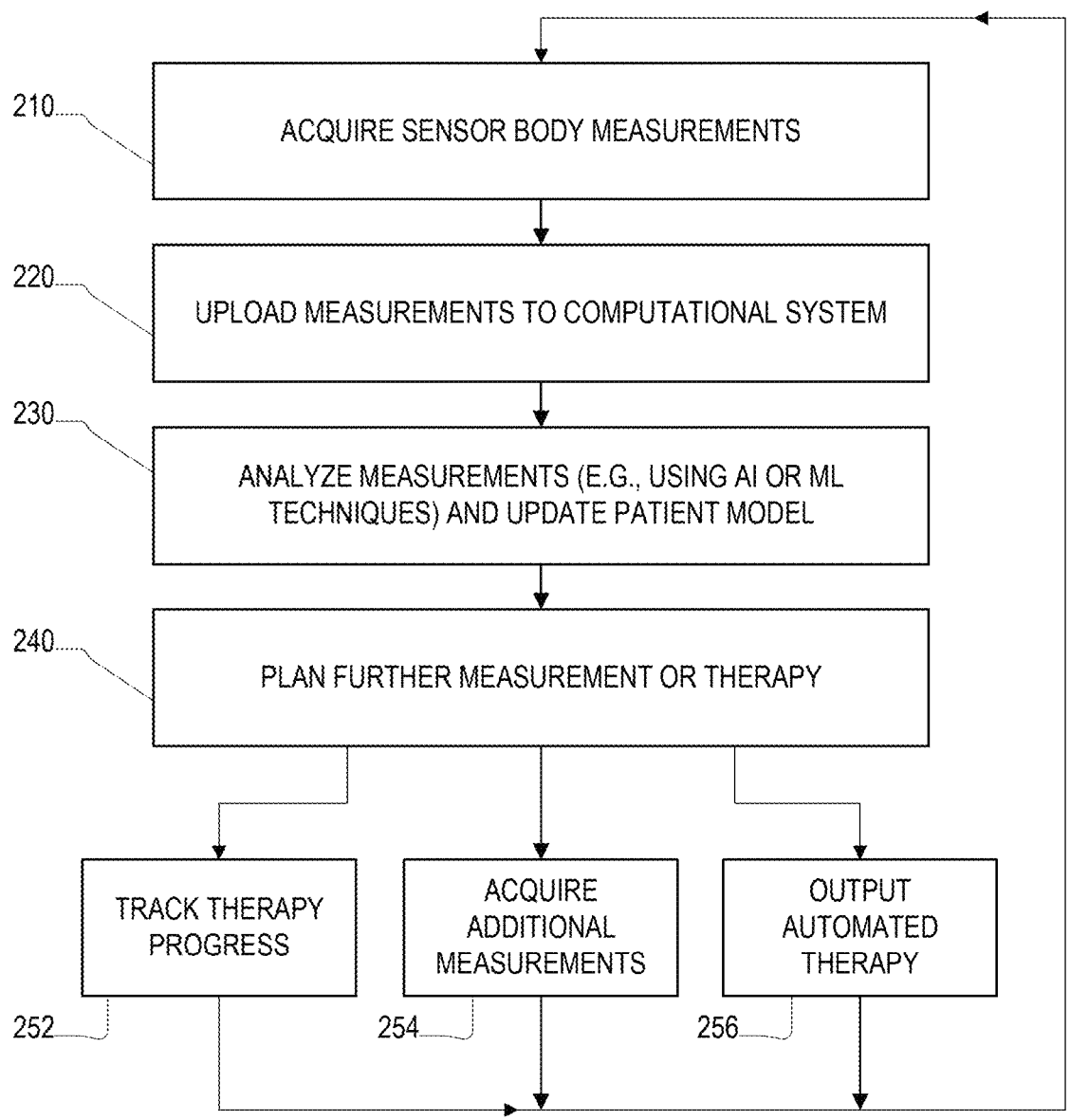
FIG. 2 is a flowchart illustrating operating modes of the system.

In various embodiments, the system 100 supports various operating modes. Referring to the flowchart in FIG. 2, some operating modes involve a closed loop feedback approach in which sensor body measurements are acquired (step 210). For example, skin conductivity and hormone levels in sweat are acquired. These measurements are uploaded to the computational system (step 220). The computational system then analyzes the measurements, for example, updating a patient model that characterizes the state of the subject (step 230). Based on the updated state of the patient, the computational system plans or performs further analysis, measurement and/or therapy for the subject (step 240). For example, the system tracks longer term progress of a subject's therapy (step 252), plans to acquire additional measurements (step 254), or causes an output of an automated therapy (step 256). This process repeats, thereby achieving a continual monitoring and optional feedback to the subject.

In some examples, a human (e.g., a clinician) is involved in the process, for example receiving output from the computational system reflecting the tracking of the subject's progress or providing input that controls or affects the therapy output to the subject.

In some implementations the computational system makes use of various machine learning techniques in performing its functions. For example, data sets tracking the progress of long term therapy sequences with patients are used to training machine learning systems to predict a most effective next therapeutic output or additional sensor measurement. In the case of automated talk therapy, the system includes a text generation and audio synthesis subsystem, where the text generation is based on a data set of human generated therapy, which the system automatically adapts to the particular subject's model.

Figure 3:
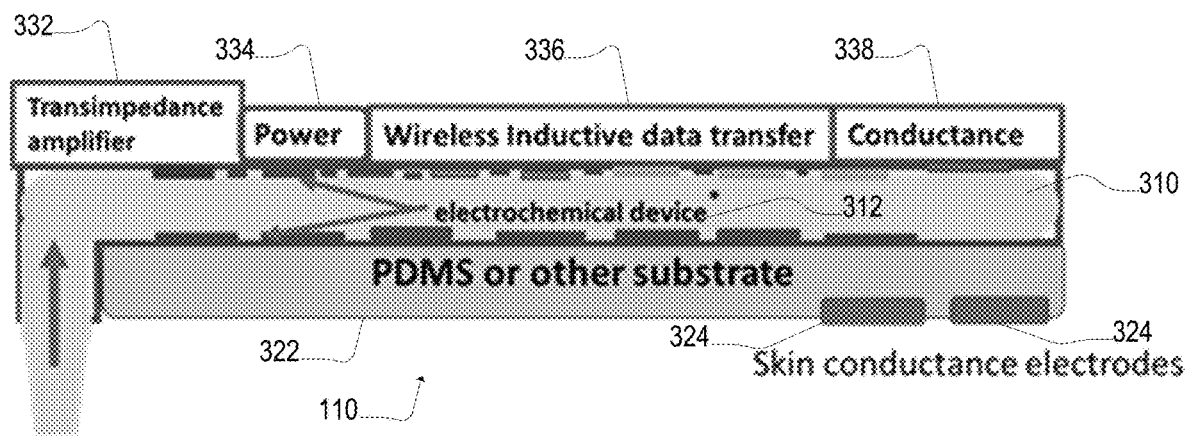
FIG. 3 is a diagram of a sensor subsystem.

Referring to FIG. 3, in one embodiment of the sensor 110 has a flexible substrate 322, and low-cost, fast and efficient biosensor (e.g., biochemical sensor 322) which operates in real-time wirelessly. In some embodiments, a polymer substrate such as polyethylene terephthalate (PET), polyethylene napthalate (PEN), polycarbonate (PC), polyethersulfone (PES), polyimide (PI), Kapton E, polycyclic olefin (PCO), polyarylates (PAR), polydimethylsiloxanes (PDMS) or flexible polyurethane membrane containing laser etched inlets and chamber where we deposit a mixture of graphene-conductive polymer through spin coating/inkjet printing/electrooxidation.

The sensor has two electrodes 324 placed on the skin on top of sweat glands. The electrodes have dual purpose. These can either be used to measure skin conductance or can be activated by reverse iontophoresis to extract interstitial fluid to the surface of the skin. Electrodes are comprised of conductive polymer layers for example PEDOT:PSS (<1 micron thick) coated with a self-assembled monolayer (SAM) of <5 nm. Choice of the SAM can be ionic liquids, hexadecyl-phosphonic acid (HDPA) that will make the surface hydrophobic and passive and create stable electrode surfaces in body fluids. These electrodes are connected to the conductance measurements electronics comprised of a Wheatstone bridge and a microcontroller circuit for the conductance measurement or to perform the reverse iontophoresis.

In some examples, the conjugated polymer is an n-type semiconductor having a naphthalene-1,4,5,8-tetracarboxylic diimide (NDI) backbone and repeat units of bithiophene (T2) and is called P-90 where the side chains on the diimide unit have a ratio of 0-95:0-5 of polar glycol and nonpolar branched alkyl groups. In the case of P90 the polar glycol versus non-polar alkyl group is 90:10. This is an n-type semiconducting polymer as opposed to PEDOT:PSS which is a p-type semiconducting polymer.

The device includes multiple thin microfluidic channels 310 in PDMS with maximum thickness 500 micron and up to 5 mm long. The body fluid is drawn by surface tension in the channel. The device contains a minimum number of three electrodes that comprise an electrochemical device 312. Microelectrode sensing electrodes have the advantage of a small iR drop and the surface modification with nanotechnology provides amplification of signals and provides device sensitivity and low limit of detection.

In some embodiments, the system uses a 3-terminal device with electrodes containing graphene nanoplatelets with conjugated polymers such as PEDOT:PSS nanocomposite/SAM/enzyme, antibody or aptamer.

In some embodiments, the system uses a molecularly imprinted graphene nanoplatelets/PEDOT:PSS polymer with an enzyme, antibody or aptamer for bio-recognition. The PEDOT:PSS is polymerized with the graphene nanoplatelets and with the biorecognition element so that these become embedded in the polymer matrix but it also is part of the polymer surface.

Two of the electrodes are comprised by a thin PEDOT: PSS nanocomposite (<1 micron) and the other which acts as a reference electrode, is comprised of a thin film metallic reference electrode made out of Ag/AgCl, TiN, Ti. Electrodes are coated by <5 nm SAM layer of hexadecyl-phosphonic acid (HDPA) which makes the surface hydrophobic and passive and creates stable electrode surfaces in body fluids.

The biorecognition element is different depending on the compound that is to be identified. For example, for cortisol an anti-CAB antibody is used. Epinephrine, norepinephrine and serotonin can be oxidized electrochemically by applying a voltage sweep between two electrodes at a rate of 50 mV/s to 1000 mV/s and measuring the resulting current. However, epinephrine and norepinephrine metabolize to vanillylmandelic acid and so their concentration in the peripheral body fluids is extremely low to be detected. Vanillylmandelic acid can be present in the urine as a product of the catecholamine metabolism. Catecholamines are present in the interstitial fluid, a fluid more representative of the blood consistency. IL-6 is detected using an IL-6 antibody and antigen and neuropeptide NPY with an anti-neuropeptide Y monoclonal antibody Y.

In some embodiments, the sensor includes electronic components, including an amplifier 332 for the sensors, a power unit 334 (e.g., including a battery), wireless data transfer electronics 336, and skin conductance measurement electronics 338.

Figure 4:
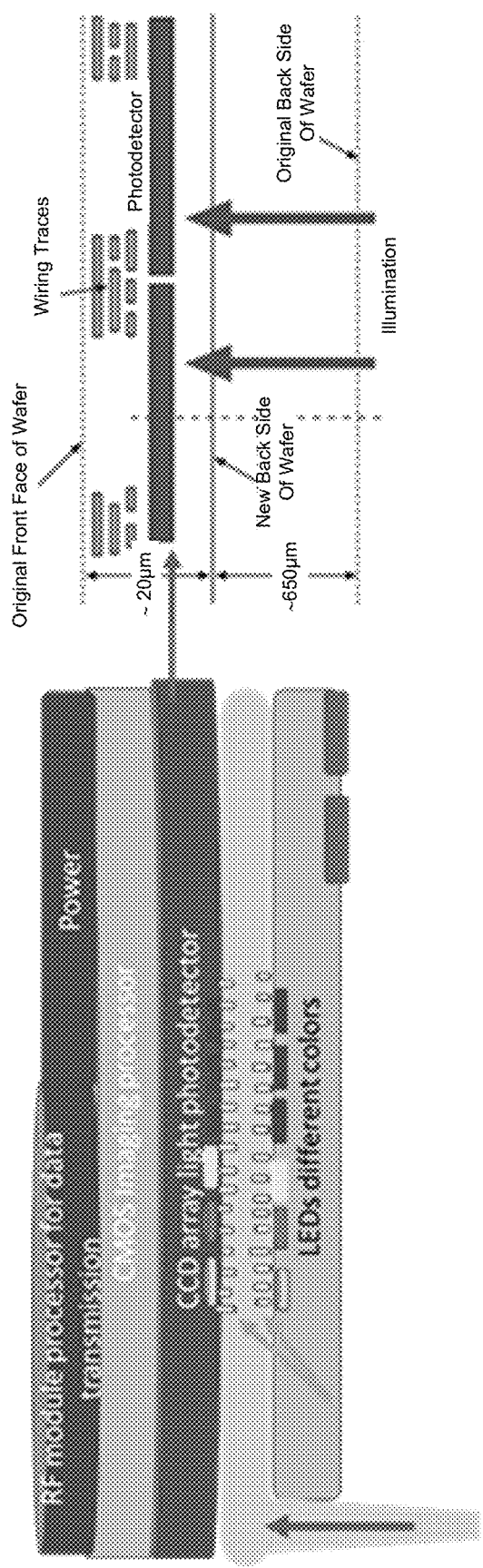
FIG. 4 is a diagram of another embodiment of the sensor subsystem.

Referring to FIG. 4 an embodiment of a sensor subsystem makes use of Raman spectroscopy. Raman spectroscopy is a non-destructive technique for the optical identification of biological compounds. Surface enhanced Raman spectroscopy achieves enhancement of the Raman vibrational signal when the molecules are attached or are near a nanostructured metal surface. The device for Raman detection of the biomolecules is shown in FIG. 4. Similarly to the device shown in FIG. 3, the optical sensor device is comprised of a flexible substrate, low-cost, fast and efficient biosensor which operates in real-time wirelessly and it is built on a polymer substrate such as polyethylene terephthalate (PET), polyethylene napthalate (PEN), polycarbonate (PC), polyethersulfone (PES), polyimide (PI), Kapton E, polycyclic olefin (PCO), polyarylates (PAR), polydimethylsiloxanes (PDMS) or flexible polyurethane membrane containing laser etched inlets and a microfluidics channel.

The sensor element is comprised of a metallic nanostructure with dimensions ≤100 nm in terms of height and width, is comprised of either PEDOT:PSS/Ti/Au, PEDOT:PSS/Ti/Ag, PEDOT:PSS/Ti/Pt, PEDOT:PSS/Ti/Ru, PEDOT:PSS/Ti/Pd or other appropriate noble metal. In contrast to the electrochemical method that requires in some cases the use of biorecognition elements such as enzymes, antibodies and aptamers, the SERS method is label free.

The device includes LEDs that provide excitation wavelengths for the detection of specific compounds. For example, cortisol requires an excitation wavelength of 638 nm, IL-6 requires a 632 nm excitation, whereas the NPY requires an excitation at 785 nm. Materials needed to excite at the red and near infrared spectrum (NIR) spectrum are GaAs (743 nm) and AlGaAs (625-760 nm) for the red GaAsP (600-625 nm) for the orange, AlGaInP (577-600 nm) for the yellow, GaN (492-577 nm) and ZnSe (455-492 nm) for the green and blue LEDs and InGaN, InAlGaN (280 nm-455 nm) for the violet LEDs.

Figure 5:
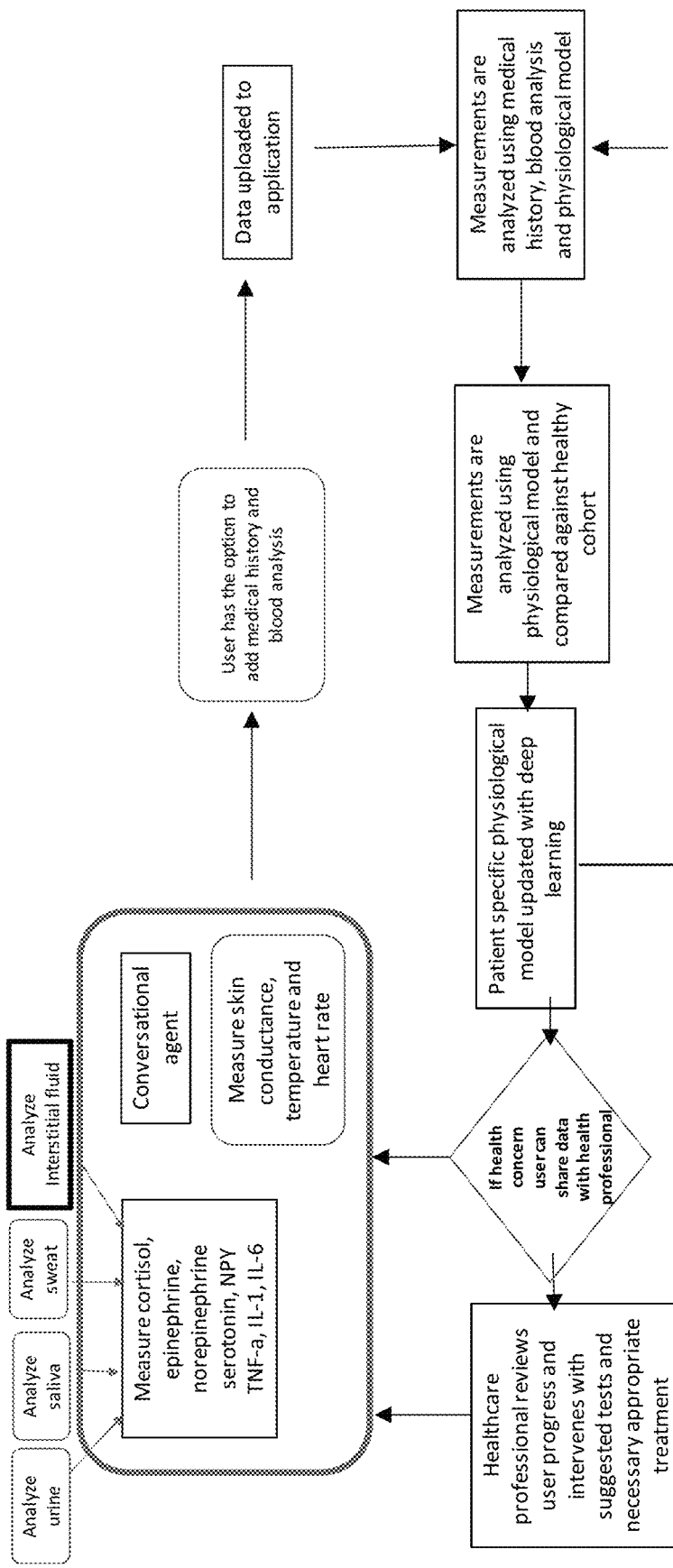
FIGS. 5-6 are flowcharts showing other operating modes of the system.

FIG. 5 is an illustrative flowchart of one operating mode. The biosensor analysis and physiological user's data, including results of any analysis of the speech from the conversational agent, are considered to build the user's model. The user has also the option to add blood analysis or other medical data to be considered in the model. Training of the model is done in the cloud with a patient database that compares the analysis and conversational patient data for different disease conditions including mood disorders such as anxiety, melancholic depression, obsessive compulsive disorder, anorexia nevrosa, excessive exercise, drug withdrawal, chronic alcoholism, post-traumatic stress disorder (PTSD), sleep-disorders, atypical depression, chronic fatigue syndrome, fibromyalgia and other disorders such as hyperthyroidism, diabetes, hypothyroidism and rheumatoid arthritis. The model is updated based on the new information provided for each user and based on the physician input and treatment plan for each user.

Figure 6:
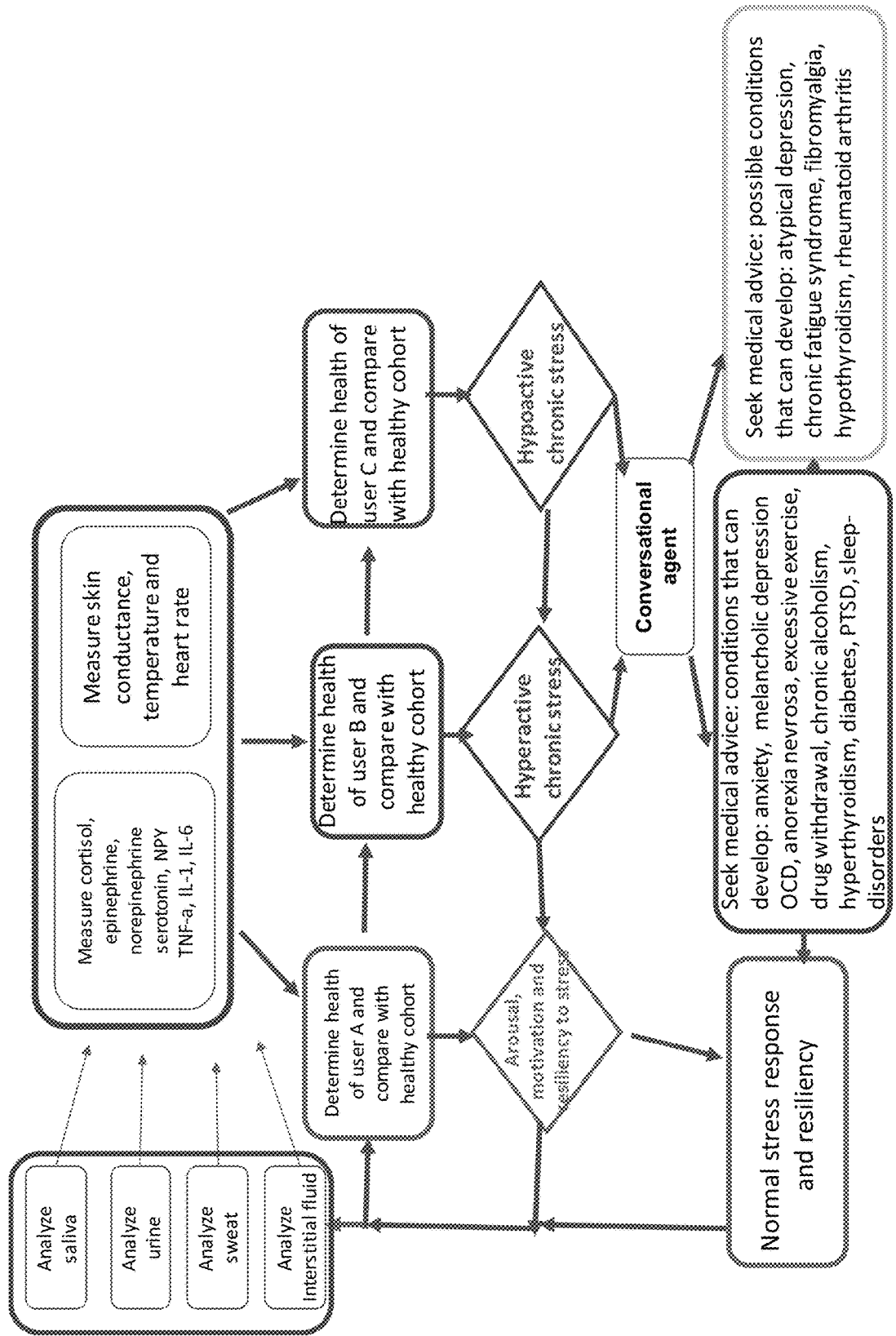

FIG. 6 is an illustrative flowchart of a process for assisting a doctor in diagnosis and objective assessment effectiveness of treatment. In one exemplary use, following the analysis of the stress and inflammation biomarkers the system determines whether the user's stress response is healthy, when the markers fall within the normal range, or in turn the stress response is defective. If the evening cortisol level is high, the levels of epinephrine, norepinephrine, TNF-a, IL-1, IL-6 are high then the system determines that the user's stress system is hyper-active and engages the conversational agent in order to determine higher probability for a more specific diagnosis among the possible disease conditions for hyper-active stress. If in turn the cortisol levels are low to normal and epinephrine, norepinephrine are lower than normal, and some of the inflammatory markers TNF-a, IL-1, IL-6 are higher than normal, the system determines that the user's stress system is hypoactive. In this case, the conversational agent is engaged with the user in order to determine an improved diagnosis among the possible disease conditions of hypo-active stress.

Implementations of one or more subsystems may make use of software that includes instructions stored on a non-transitory machine-readable medium. These instructions, when executed by a computer processor, cause the system to perform steps outlined above. Some implementations may make use of hardware, including custom circuitry (e.g., Application Specific Integrated Circuits, ASICs, or Field Programmable Gate Arrays, FPGAs), and yet other implementations may use a combination of hardware and software.

It is to be understood that the foregoing description is intended to illustrate and not to limit the scope of the invention, which is defined by the scope of the appended claims. Other embodiments are within the scope of the following claims.

What is claimed is:

1. A biosensing system comprising:
   a non-invasive sensor subsystem and
   a computation subsystem in communication with the sensor subsystem;
   wherein the non-invasive sensor subsystem is affixable to skin of a subject and includes a plurality of sensors, including a biofluid sensor and one or more of a skin surface sensor and an audio sensor, the skin surface sensor including a sensor for at least one of skin conductance, temperature, heart rate, and response of the nervous system, the biofluid sensor including a nanotechnology-based optical sensor for measuring biomarkers of stress and inflammation, wherein the non-invasive sensor subsystem comprises at least one electrode placeable on the skin of the subject, and configured to both: i) extract interstitial fluids containing the biomarkers of stress and inflammation from the of the subject through reverse iontophoresis for delivery to the optical sensor of the biofluid sensor and ii) measure skin surface properties;
   wherein the computation subsystem implements a closed loop feedback approach configured to receive sensor measurements acquired at the sensor subsystem from the subject and process the measurements to determine an updateable psychiatric disorder model of the subject, the computation subsystem being configured to monitor effectiveness of behavioral therapy and/or a drug-based therapy provided to the subject to treat one or more psychiatric disorders, the updateable psychiatric disorder model being a machine learning model trained to perform long-term continuous real-time predictions of actionable outputs that include one or more of a therapeutic output controllably provided to the subject and an additional required sensor measurement controllably performed by the sensor subsystem to further update the psychiatric disorder model based on the additional required sensor measurement; and
   wherein the computation subsystem that implements the closed loop feedback approach is configured to:

determine if measured levels of compounds detected in the extracted interstitial fluids or levels of the skin surface properties are abnormal compared to those of a healthy cohort;

in response to a determination of abnormal levels of detected compounds or abnormal levels of the skin surface properties, engage in a conversation with the subject to receive verbal responses to one or more medical questions;

and compute probabilities of one or more medical or psychiatric conditions, the probabilities falling within a range of [0, 1], and/or determine the actionable outputs based on the levels of detected compounds or the levels of the skin surface properties, and further based on an analysis of the verbal responses to the one or more medical questions.

2. The system of claim 1, wherein the computation subsystem is further configured to provide information to a clinician based on the updateable psychiatric disorder model of the subject.

3. The system of claim 1, wherein the computation subsystem is further configured to cause output to be presented to the subject, including at least one of a speech-based therapy, the drug-based therapy, and an electrical stimulation therapy.

4. The system of claim 1, wherein the computation subsystem is further configured to cause acquisition of additional measurements by the sensor subsystem.

5. The system of claim 1, wherein the computation subsystem is configured to determine that additional measurements are required based on the updateable mental state model of the subject.

6. The system of claim 1, wherein the computation subsystem is further configured to solicit information from the subject.

7. The system of claim 1, wherein the computation subsystem is further configured to prompt the subject with a voice prompt and to acquire a voice response from the subject.

8. A biosensing system comprising:
a sensor subsystem and
a computation subsystem in communication with the sensor subsystem;
wherein the sensor subsystem includes a plurality of sensors, including a biofluid sensor and one or more of a skin surface sensor and an audio sensor, the skin surface sensor including a sensor for at least one of skin conductance, temperature, heart rate and response of the nervous system, the biofluid sensor including a nanotechnology-based electrochemical sensor for measuring biomarkers of stress and inflammation;
wherein the computation system is configured to receive sensor measurements acquired at the sensor subsystem from an individual and process the measurements to determine a model of the individual; and
wherein the plurality of sensors includes a biosensor for use with the individual, the biosensor comprising:
a nanotechnology-based electrochemical device for measuring biomarkers of at least one of stress and inflammation in at least one of peripheral fluids and in interstitial fluid;
a nanotechnology-based optical device for determining a level of at least one of stress and inflammation of the individual; and
a skin sensor comprising one or more electrodes placed on a skin-touching surface of a substrate of the sensor subsystem, the one or more electrodes configured to perform measurement of at least one of conductance, temperature, heart rate and the response of the nervous system, wherein the one or more electrodes are further configured to cause reverse iontophoresis to extract the interstitial fluid to a surface of the skin of the individual and wherein the extracted interstitial fluid or sweat is delivered to a first microfluidic channel of the optical device for Raman spectroscopy analysis performed on the extracted interstitial fluid and to a second microfluidic channel of the electrochemical device to perform biorecognition analysis on the extracted interstitial fluid or sweat.

9. The system of claim 8, wherein the biosensor further comprises a communication element for wirelessly communicating measurements made at the biosensor to the computation system, wherein the computation system is implemented remotely at a wireless device.

10. The system of claim 8, wherein the biosensor further comprises an audio sensor for acquiring acoustic signals including the individual's speech.

11. The system of claim 8, wherein the biosensor further comprises means for conducting a computer-controlled conversation with the individual based on measurements made at the biosensor.

12. The system of claim 8, wherein the biosensor further comprises a communication element for sending measurements made at the biosensor to the computation system, for sending data based on the individual's speech to the computation system, and for receiving data representing speech output to the presented to the individual.

13. A biosensing system comprising: a non-invasive sensor subsystem and a computation subsystem in communication with the sensor subsystem; wherein the non-invasive sensor subsystem includes a plurality of sensors, including a biofluid sensor and one or more of a skin surface sensor to measure skin surface properties and an audio sensor, the skin surface sensor including a sensor for at least one of skin conductance, temperature, heart rate, and response of the nervous system, the biofluid sensor including a nanotechnology-based electrochemical sensor for measuring biomarkers of stress and inflammation; wherein the computation system is configured to receive sensor measurements acquired at the sensor subsystem from an individual and process the measurements to determine an updateable psychiatric disorder model of the individual, configured to monitor effectiveness of behavioral therapy provided to the individual; and wherein the plurality of sensors includes a biosensor affixed to the individual's skin for use with the individual, the biosensor comprising: a nanotechnology-based optical device, placed on the biosensor affixed to the individual's skin, for non-invasively extracting interstitial fluid and determining a level of at least one of stress and inflammation of the individual; and a skin sensor comprising one or more electrodes placed on a skin-touching surface of a substrate of the sensor subsystem, the one or more electrodes configured to perform measurement of at least one of conductance, temperature, heart rate and the response of the autonomous nervous system, wherein the one or more electrodes cause reverse iontophoresis to extract the interstitial fluid to a surface of the skin of the individual, wherein the extracted interstitial fluid or sweat is delivered to one or more microfluidic channels of the sensor subsystem for Raman spectroscopy analysis performed on the extracted interstitial fluid or sweat; wherein the computation subsystem that implements the closed loop feedback approach is configured to:

determine if measured levels of compounds detected in the extracted interstitial fluids or levels of the skin surface properties are abnormal compared to those of a healthy cohort;

in response to a determination of abnormal levels of detected compounds or abnormal levels of the skin surface properties, engage in a conversation with the subject to receive verbal responses to one or more medical questions;

and compute probabilities of one or more medical or psychiatric conditions, the probabilities falling within a range of [0, 1], and/or determine the actionable outputs based on the levels of detected compounds or the levels of the skin surface properties, and further based on an analysis of the verbal responses to the one or more medical questions.

14. The system of claim 13, wherein the biosensor further comprises: a communication element for communicating measurements made at the biosensor to the computation system.

15. The system of claim 13, wherein the biosensor further comprises: an audio sensor for acquiring acoustic signals including the individual's speech.

16. The system of claim 13, wherein the biosensor further comprises means for conducting a computer-controlled conversation with the individual based on measurements made at the biosensor.

17. The system of claim 13, wherein the biosensor further comprises a communication element for sending measurements made at the biosensor to the computation system, for sending data based on the individual's speech to the computation system, and for receiving data representing speech output to the presented to the individual.

18. The system of claim 1, wherein the system is further configured for computer-controlled diagnosis, treatment, and/or monitoring of treatment, wherein the computation subsystem is further configured to determine information comprising at least one of diagnosis information, treatment information, and treatment monitoring information from the measurements acquired from the sensor subsystem.

19. The system of claim 1, wherein the sensor subsystem is configured to acquire the measurements repeatedly or substantially continuously.

20. The system of claim 8, wherein the nanotechnology-based optical device for determining the level of at least one of stress and inflammation of the individual includes a nanotechnology-based optical device to perform the Raman spectroscopy analysis to identify biological compounds in the body of the individual used for determining the level of stress or inflammation of the individual.

21. The system of claim 1, wherein the non-invasive sensor subsystem comprises a multi-layer device that includes a substrate with a first surface affixable to the skin of the subject and a microfluidic layer disposed on a second surface of the substrate, opposite the first surface, the microfluidic layer including one or more microfluidic channels to analyze interstitial fluid non-invasively extracted through the skin of the individual, wherein each of the one or more microfluidic channels has a maximum thickness of five hundred microns and up to five millimeters in length that cause the interstitial fluid to be drawn through surface tension along the microfluid channels.

22. The system of claim 21, wherein the non-invasive sensor subsystem further comprises one or more electrodes disposed on the first surface of the substrate affixable to the skin of the subject, the one or more electrodes configured to measure at least one of conductance, temperature, heart rate, and the response of the nervous system, and to cause reverse iontophoresis to extract the interstitial fluid to a surface of the skin of the subject, wherein the extracted interstitial fluid or sweat is delivered to the one or more microfluidic channels.

23. The system of claim 21, wherein the one or more microfluidic channels include at least one of: a first microfluidic channel to perform Raman spectroscopy analysis on the interstitial fluid or sweat, wherein the first microfluid channel is lined with LED devices to emit optical radiation at pre-determined wavelengths that cause excitation of specific compounds, the LED devices being used with at least one optical sensor to determine if a cortisol compound is detected in the extracted interstitial fluid or sweat, wherein the LED devices include two or more of: a GaAs LED device emitting at 743 nm wavelength, AlGaAs LED device emitting at 625-760 nm wavelength, GaAsP LED device emitting at 600-625 nm wavelength, AlGaInP LED device emitting at 577-600 nm wavelength, GaN LED device emitting at 492-577 nm wavelength, ZnSe LED device emitting at 455-492 nm wavelength, InGaN or InAlGaN LED device emitting at 280 nm-455 nm wavelength; and a second microfluidic channel configured to perform electrochemical and biorecognition analysis on compounds in the extracted interstitial fluid or sweat.

\* \* \* \* \*